United States Patent
Choi et al.

(10) Patent No.: US 9,663,426 B2
(45) Date of Patent: May 30, 2017

(54) COMPOSITE METAL CATALYST COMPOSITION, AND METHOD AND APPARATUS FOR PREPARING 1,4-CYCLOHEXANEDIMETHANOL USING SAME

(71) Applicant: LOTTE CHEMICAL CORPORATION, Seoul (KR)

(72) Inventors: Young Heon Choi, Daejeon (KR); Hyun Woo Park, Daejeon (KR); Sung Joon Park, Daejeon (KR); Seong Hwan Choi, Daejeon (KR); Mi Sun Cha, Daejeon (KR); Seong Min Kim, Daejeon (KR); Young Jong Seo, Daejeon (KR)

(73) Assignee: LOTTE CHEMICAL CORPORATION, Seoul (KR)

( * ) Notice: Subject to any disclaimer, the term of this patent is extended or adjusted under 35 U.S.C. 154(b) by 0 days.

(21) Appl. No.: 15/128,308

(22) PCT Filed: Apr. 7, 2015

(86) PCT No.: PCT/KR2015/003476
§ 371 (c)(1),
(2) Date: Sep. 22, 2016

(87) PCT Pub. No.: WO2015/156582
PCT Pub. Date: Oct. 15, 2015

(65) Prior Publication Data
US 2017/0107164 A1    Apr. 20, 2017

(30) Foreign Application Priority Data

Apr. 7, 2014 (KR) .................. 10-2014-0041322
Oct. 23, 2014 (KR) .................. 10-2014-0144233
Nov. 11, 2014 (KR) .................. 10-2014-0156335
Nov. 11, 2014 (KR) .................. 10-2014-0156345

(51) Int. Cl.
| | |
|---|---|
| C07C 29/00 | (2006.01) |
| B01J 8/00 | (2006.01) |
| B01J 23/00 | (2006.01) |
| C07C 29/149 | (2006.01) |
| B01J 23/42 | (2006.01) |
| B01J 23/62 | (2006.01) |
| B01J 29/12 | (2006.01) |
| B01J 8/04 | (2006.01) |

(52) U.S. Cl.
CPC ........... *C07C 29/149* (2013.01); *B01J 8/0492* (2013.01); *B01J 8/0496* (2013.01); *B01J 23/42* (2013.01); *B01J 23/626* (2013.01); *B01J 29/126* (2013.01); *B01J 2208/00017* (2013.01); *C07C 2101/14* (2013.01)

(58) Field of Classification Search
CPC ....... C07C 29/149; B01J 8/0492; B01J 23/42; B01J 23/44; B01J 23/626; B01J 2208/00017
See application file for complete search history.

(56) References Cited

U.S. PATENT DOCUMENTS

| | | |
|---|---|---|
| 6,294,703 B1 | 9/2001 | Hara et al. |
| 6,600,080 B1 | 7/2003 | Nagamura et al. |

FOREIGN PATENT DOCUMENTS

| | | |
|---|---|---|
| EP | 0934920 A2 | 8/1999 |
| EP | 1090902 A2 | 4/2001 |
| JP | 5-132681 A | 5/1993 |
| JP | 7-188079 A | 7/1995 |
| JP | 2000-007596 A | 1/2000 |
| JP | 2001-181223 A | 7/2001 |
| JP | 2002-145824 A | 5/2002 |
| JP | 4513256 B2 | 7/2010 |
| JP | 2010-270093 A | 12/2010 |
| KR | 10-2007-0100754 A | 10/2007 |
| KR | 10-1073067 B1 | 10/2011 |

OTHER PUBLICATIONS

International Search Report for PCT/KR2015/003476 mailed Jul. 17, 2015 from Korean Intellectual Property Office.
Morris Freifelder, et al., "Low-Pressure Hydrogenation of Some Benzenepolycarboxylic Acids with Rhodium Catalyst", The Journal of Organic Chemistry, 1966, pp. 3438-3439, vol. 31(10).
Tahara K, et al., "Liquid-Phase Hydrogenation of Carboxylic-Acid on Supported Bimetallic Ru—Sn-Alumina Catalysts", Applied Catalysis A: General, 1997, pp. 75-86, vol. 154, No. 1-2.
Tomohiro Maegawa, et al., "Efficient and Practical Arene Hydrogenation by Heterogeneous Catalysts under Mild Conditions", Chemistry A European Journal, Jul. 13, 2009, pp. 6953-6963, vol. 15, Issue 28.

*Primary Examiner* — Sikarl Witherspoon
(74) *Attorney, Agent, or Firm* — Paratus Law Group, PLLC

(57) ABSTRACT

Disclosed are a composite metal catalyst composition capable of increasing efficiency and economic feasibility of a reaction through simplification of a reaction process, and providing 1,4-cyclohexanedimethanol with high purity for a shorter time while minimizing byproducts; and a method and apparatus for preparing 1,4-cyclohexanedimethanol with high purity using the same. The present invention provides a composite metal catalyst composition for converting an aromatic dicarboxylic acid into an alicyclic diol compound, the composition containing: a first metal catalyst including a palladium (Pd) compound; and a second metal catalyst including a ruthenium (Ru) compound, a tin (Sn) compound, and a platinum (Pt) compound, and a method and apparatus for preparing 1,4-cyclohexanedimethanol using the same.

20 Claims, 1 Drawing Sheet

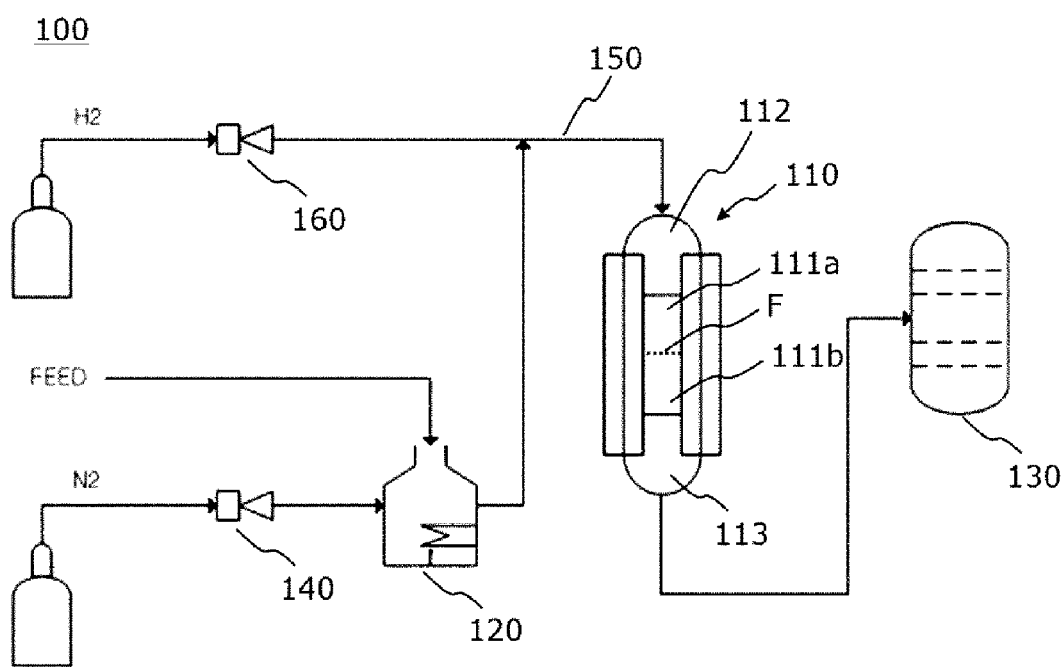

COMPOSITE METAL CATALYST COMPOSITION, AND METHOD AND APPARATUS FOR PREPARING 1,4-CYCLOHEXANEDIMETHANOL USING SAME

CROSS REFERENCE TO PRIOR APPLICATIONS

This application is a National Stage Patent Application of PCT International Patent Application No. PCT/KR2015/003476 (filed on Apr. 7, 2015) under 35 U.S.C. §371, which claims priority to Korean Patent Application Nos. 10-2014-0041322 (filed on Apr. 7, 2014), 10-2014-0144233 (filed on Oct. 23, 2014), 10-2014-0156335 (filed on Nov. 11, 2014), and 10-2014-0156345 (filed on Nov. 11, 2014), which are all hereby incorporated by reference in their entirety.

TECHNICAL FIELD

The present invention relates to a composite metal catalyst composition, and a method and an apparatus for preparing 1,4-cyclohexanedimethanol using the same, and more particularly, to a composite metal catalyst composition, which may increase efficiency and economic efficiency of a reaction by further simplifying a reaction process and may provide high purity 1,4-cyclohexanedimethanol in a shorter period of time while minimizing by-products, and a preparation method and an apparatus which may provide high purity 1,4-cyclohexanedimethanol using the composite metal catalyst composition.

BACKGROUND ART

A conventional method of preparing 1,4-cyclohexanedimethanol may be categorized into two methods. One method is a method of synthesizing 1,4-cyclohexanedimethanol through 1,4-dimethyl cyclohexane dicarboxylate under high-temperature and high-pressure conditions using dimethyl terephthalate, and the other method is a method of synthesizing 1,4-cyclohexanedicarboxylic acid using terephthalic acid and preparing 1,4-cyclohexanedimethanol therefrom.

However, the previously known methods of preparing 1,4-cyclohexanedimethanol may be uneconomical in that an additional process for removing or recovering by-products generated during process commercialization or catalysts used in each step may be required. Thus, there is a need to develop an efficient method which compensates these limitations by simplifying a reaction process, prepares 1,4-cyclohexanedimethanol from terephthalic acid which is known that hydrogenation is difficult, and simultaneously reduces reaction time and by-products.

The present invention is a technique of preparing 1,4-cyclohexanedimethanol from terephthalic acid in a sequential manner using a hydrogenation catalyst in a single reactor, wherein there is no direct prior art, but some prior arts are summarized as follows.

Japanese Patent Application Laid-Open Publication No. 2002-145824 discloses a method of preparing 1,4-cyclohexanedimethanol in which terephthalic acid is hydrogenated in the presence of a solvent and a palladium catalyst, 1,4-cyclohexanedimethanol, as an intermediate, is obtained, and hydrogenation is then further performed thereon. However, by-products are generated in this method to reduce selectivity of the finally prepared 1,4-cyclohexanedimethanol, and accordingly, it is disadvantageous in that higher aliphatic alcohol, such as 2-ethylhexanol, is used as an extraction agent or processes of separating and recovering the generated by-products and alcohol are required.

European Patent No. 0934920 discloses a preparation method in which a Raney catalyst is prepared to reduce terephthalic acid, but, since this method uses the catalyst, which is not easy to be commercialized in a large scale, and uses dioxane as well as water as a reaction solvent, separation and recovery processes for each component may be required. Thus, its application area may be limited.

U.S. Pat. No. 6,294,703 discloses a method of synthesizing 1,4-cyclohexanedimethanol from 1,4-cyclohexanedicarboxylic acid using a composite catalyst impregnated with ruthenium and tin, but it is difficult to sufficiently secure the selectivity of the finally prepared 1,4-cyclohexanedimethanol and, since a base must be used during hydrogenation, a separate and additional process or cost for processing the base in a commercialization process may be required and environmental problems may also occur.

With respect to a conventional method of preparing 1,4-cyclohexanedimethanol, purity or reaction efficiency of the finally obtained 1,4-cyclohexanedimethanol is not very high. Also, since solubility of terephthalic acid among reactants in water is low, a salt of metal, such as alkali metal, must be prepared and reacted to increase reactivity when water is used as a solvent. Thus, in order to obtain trans-1,4-cyclohexanedimethanol as a final product, it is inconvenient that the metal of the metal salt must be substituted with a hydrogen ion by an acid treatment. Furthermore, in cis/trans-mixed-1,4-cyclohexanedimethanol, caution is required because there is a tendency that the higher the ratio of the trans-1,4-cyclohexanedimethanol is, the more the dissolution temperature in water, as the solvent, increases.

Korean Patent No. 1073067 discloses a technique in which dimethyl 1,4-cyclohexane dicarboxylate (DMCD) is used as a raw material and 1,4-cyclohexanedicarboxylic acid (CHDA) is prepared and recrystallized by hydrolysis in a solvent, but, since an ion exchange resin, in which a restrictive reaction condition is disadvantageous, and an acid catalyst, such as paratoluenesulfonic acid (p-TSA), are used, neutralization equipment and process may be additionally required.

Japanese Patent No. 4513256 discloses a technique in which cis-1,4-cyclohexanedicarboxylic acid (c-CHDA) is heated at a melting point of 300° C. or more and then crystallized to be precipitated into trans-1,4-cyclohexanedicarboxylic acid (t-CHDA), but, when the above condition is commercialized, it is inconvenient that the high temperature must be maintained for 1 hour or more, and purification/separation equipment may be required.

Japanese Patent Application Laid-Open Publication No. 2010-270093 discloses a method of preparing trans-1,4-cyclohexanedicarboxylic acid dimethyl (HDMT) from cis/trans mixed-1,4-cyclohexanedicarboxylic acid dimethyl by processes I and II using a catalyst, but the HDMT is a material for preparing trans-1,4-cyclohexanedicarboxylic acid (t-CHDA), wherein process equipment must be additionally installed in comparison to the known method, and separate neutralization equipment may be required due to base catalysis.

Non-Patent Document 1 (Journal of Organic Chemistry, 31(10), 3438-9, 1996) discloses a method in which terephthalic acid is hydrogenated in an aqueous solution in the presence of a rhodium and alumina catalyst under conditions including a temperature of 60° C. to 70° C. and a hydrogen pressure of 3 kg/cm$^2$ or less, the obtained reactant is extracted with chloroform after the catalyst is removed from the reactant by high-temperature filtration, and 1,4-cyclohexanedimethanol is obtained in a yield of 90%, but, since the chloroform is used as an extraction solution after the reaction, environmental issues are generated and additional recovery equipment is required, and thus, there is a limitation in using the method.

Non-Patent Document 2 (Applied Catalysis A: General 154 (1997) 75-86) discloses a method of obtaining 90% or more of 1,4-cyclohexanedimethanol at 230° C. and 100 kg/cm$^2$ using Ru—Sn metal, but, since there is a disadvantageous in that a yield of cyclohexanedimethanol is rapidly decreased when the number of reuses of the catalyst is greater than 5 times, its practical application may be difficult.

Non-Patent Document 3 (Chem. Eur J. 2009, 15, 6953-6963) discloses a method of obtaining 1,4-cyclohexanedicarboxylic acid by reacting terephthalic acid at 60° C. and 100 kg/cm$^2$ for 24 hours using a ruthenium catalyst, but, since the reaction time is excessively long and lithium aluminum hydride (LiAlH$_4$), as an alkali metal in which commercialization of the process is difficult, is used, its application may be difficult.

DISCLOSURE OF THE INVENTION

Technical Problem

The present invention provides a composite metal catalyst composition, which may increase efficiency and economic efficiency of a reaction by further simplifying a reaction process and may provide high purity 1,4-cyclohexanedimethanol in a shorter period of time while minimizing by-products, and a method and an apparatus which may prepare high purity 1,4-cyclohexanedimethanol using the composite metal catalyst composition.

The present invention also provides a method and an apparatus which may overcome the above-described limitations, may prepare high purity trans-1,4-cyclohexanedimethanol in a high yield while reducing a known two-step process to one step, and may prepare desired trans-1,4-cyclohexanedimethanol by adjusting a ratio between cis and trans isomers in a method of preparing trans-1,4-cyclohexanedimethanol by reducing terephthalic acid.

Technical Solution

According to an aspect of the present invention, there is provided a composite metal catalyst composition which converts an aromatic dicarboxylic acid to an alicyclic diol compound by including a first metal catalyst including a palladium (Pd) compound; and a second metal catalyst including a ruthenium (Ru) compound, a tin (Sn) compound, and a platinum (Pt) compound.

According to another aspect of the present invention, there is provided a method of preparing 1,4-cyclohexanedimethanol including reducing terephthalic acid in the presence of a composite metal catalyst composition which includes a first metal catalyst including a palladium (Pd) compound; and a second metal catalyst including a ruthenium (Ru) compound, a tin (Sn) compound, and a platinum (Pt) compound.

The reducing of the terephthalic acid may be performed in the presence of the first metal catalyst, and may include reducing a reduction product of the terephthalic acid in the presence of the second metal catalyst.

The second metal catalyst may include the ruthenium (Ru) compound, the tin (Sn) compound, and the platinum (Pt) compound in a weight ratio of 1:0.8 to 1.2:0.2 to 0.6.

The reducing of the terephthalic acid and the reducing of the reduction product of the terephthalic acid may be continuously performed.

The reducing of the terephthalic acid and the reducing of the reduction product of the terephthalic acid may be performed in a single reactor.

In the reactor, the first metal catalyst and the second metal catalyst may be separately and sequentially injected into a fixed bed.

Each of the first metal catalyst and the second metal catalyst may be fixed to a support.

The first metal catalyst including the support may be used in an amount of 1 part by weight to 50 parts by weight based on 100 parts by weight of the terephthalic acid.

The second metal catalyst including the support may be used in an amount of 1 part by weight to 50 parts by weight based on 100 parts by weight of the terephthalic acid.

The second metal catalyst may include 0.5 wt % to 20 wt % of the ruthenium (Ru) compound.

The support may be a porous inorganic support having a specific surface area of 200 m$^2$/g to 900 m$^2$/g.

The support may have a total pore volume of 1.2 cm$^3$/g or less, and a volume of pores having a radius of 10 Å or less may be in a range of 0.1 cm$^3$/g to 0.8 cm$^3$/g.

The support may be Y-type zeolite.

The reducing of the terephthalic acid may be performed by contacting the terephthalic acid and hydrogen gas, and the reducing of the reduction product of the terephthalic acid may be performed by contacting the reduction product of the terephthalic acid and hydrogen gas.

The reducing of the terephthalic acid and the reducing of the reduction product of the terephthalic acid may be respectively performed in a temperature range of 50° C. to 350° C.

The reducing of the terephthalic acid and the reducing of the reduction product of the terephthalic acid may be respectively performed at a pressure of 30 bar to 150 bar.

The second metal catalyst may include the ruthenium (Ru) compound, the tin (Sn) compound, and the platinum (Pt) compound in a weight ratio of 1:0.9 to 1.1:0.3 to 0.55.

A molar ratio of trans-1,4-cyclohexanedimethanol in the finally generated 1,4-cyclohexanedimethanol may be 20% or more.

According to another aspect of the present invention, there is provided an apparatus for preparing 1,4-cyclohexanedimethanol by reducing terephthalic acid which includes a reactor including a raw material feeding unit in which terephthalic acid is transferred and introduced into a top end, a reaction section in which a reduction reaction of the terephthalic acid introduced from the raw material feeding unit is performed, and an outlet which is formed at a bottom end to allow a product generated in the reaction section to be transferred to a receiver; a preheater in which the terephthalic acid and ion exchange water are introduced to transfer dissolved terephthalic acid to the reactor by an inert gas through a mass flow controller; and the receiver which recovers the product from the outlet from which the product generated in the reaction section is discharged, wherein the reaction section includes an upper reaction section, in which a first metal catalyst including a palladium (Pd) compound is injected to perform a reduction reaction of the terephthalic acid introduced from the raw material feeding unit, and a lower reaction section in which a second metal catalyst, as a catalyst including a ruthenium (Ru) compound, a tin (Sn) compound, and a platinum (Pt) compound, is injected to form an interface with the first metal catalyst and perform a reduction reaction of a resultant product reduced in the upper reaction section.

Advantageous Effects

According to the present invention, there is an effect in which efficiency and economic efficiency of a reaction may be increased by further simplifying a reaction process and high purity 1,4-cyclohexanedimethanol may be prepared in a shorter period of time while minimizing by-products.

The conventional preparation of 1,4-cyclohexanedimethanol is based on dimethyl terephthalate and terephthalic acid, wherein, since catalyst and reaction condition used for each step are different, resultant catalytic process and separation and recovery procedures are required and a wastewater treatment issue occurs. In order to address the limitations, the present inventors have paid attention to direct hydrogenation for the simplification of the reaction using a mixed catalyst system, and concerned dissolution of catalyst poison and reduction of catalytic activity are also addressed through more than 10 times catalyst reuse experiments, leading to the demonstration of the excellence of the present invention.

Specifically, according to a method of preparing 1,4-cyclohexanedimethanol of the present invention, since almost all of reactants participate in the reaction to achieve a high conversion rate and high purity 1,4-cyclohexanedimethanol may be prepared in a shorter period of time while minimizing by-products, a relatively simplified reaction process design is possible and the efficiency and economic efficiency of the entire preparation process may be improved.

Also, since the terephthalic acid is introduced into a reactor in which a first metal catalyst including a palladium (Pd) compound and a second metal catalyst including a ruthenium (Ru) compound, a tin (Sn) compound, and a platinum (Pt) compound at an optimal content ratio are separately and sequentially injected into a fixed bed, the process is simplified so that the reduction of the terephthalic acid and the reduction of a reduction product of the terephthalic acid are continuously performed under the same process condition of the unified catalytic fixed bed in the same reactor, and thus, there is an effect of dramatically reducing the process time.

Furthermore, an additional process or step for separating and recovering by-products may be omitted by minimizing the by-products generated during the preparation of the 1,4-cyclohexanedimethanol, and a refining process for increasing purity may be omitted.

BRIEF DESCRIPTION OF THE DRAWINGS

FIG. 1 is a schematic view illustrating an apparatus, which prepares trans-1,4-cyclohexanedimethanol by reducing terephthalic acid, according to an embodiment of the present invention.

MODE FOR CARRYING OUT THE INVENTION

Hereinafter, the present invention will be described in detail, according to exemplary embodiments. It will be understood that words or terms used in the specification and claims shall not be interpreted as the meaning defined in commonly used dictionaries. It will be further understood that the words or terms should be interpreted as having a meaning that is consistent with their meaning in the context of the relevant art and the technical idea of the invention, based on the principle that an inventor may properly define the meaning of the words or terms to best explain the invention. Accordingly, since the embodiments set forth in the present specification and the configurations illustrated in the drawings are shown by way of example and do not represent all the technological spirit of the present invention, it should be understood that embodiments of the present invention are capable of various modifications, equivalents, and alternatives at the time of present application.

The present invention provides a composite metal catalyst composition which converts an aromatic dicarboxylic acid to an alicyclic diol compound by including a first metal catalyst including a palladium (Pd) compound; and a second metal catalyst including a ruthenium (Ru) compound, a tin (Sn) compound, and a platinum (Pt) compound, and the composite metal catalyst composition is particularly suitable for the preparation of 1,4-cyclohexanedimethanol which includes a step of reducing terephthalic acid.

With respect to the quality of terephthalic acid used in the present invention, high purity terephthalic acid, which has been previously used as a raw material of 1,4-cyclohexanedicarboxylic acid, may not only be used, but typical industrial-quality terephthalic acid, which has not often been used, may also be used, and it is desirable to use terephthalic acid containing small amounts of various metal ions which may affect due to catalyst poison during direct hydrogenation.

A composite metal catalyst according to the present invention may be used by being impregnated in a porous inorganic support. Since the support may act as catalyst poison due to the effect of an acid, supports, such as activated carbon, alumina, zeolite, silica, and carbon, may be used. A metal oxide, such as silica, alumina, zirconium oxide, and titanium dioxide, a composite oxide, such as silica-alumina, acidic activated carbon, and zeolite may be particularly used as a support having acidity, and, for example, acidic activated carbon and zeolite may be used. The expression "acidic activated carbon" denotes activated carbon which is acid-treated with an aqueous solution such as hydrochloric acid, sulfuric acid, phosphoric acid, perchloric acid, and hypochlorous acid. Also, a raw material of the activated carbon modified into the acidic activated carbon is not particularly limited, but lignum, coconut shell, organic polymer, petroleum pitch, and chaff may be used. A loading amount of metal loaded on the support is not particularly limited, but the metal may be loaded in an amount of 0.01 wt % to 40 wt %, particularly 0.1 wt % to 30 wt %, and more particularly 1 wt % to 20 wt % based on the support in consideration of yield and economic efficiency.

A method of preparing the composite metal catalyst is not particularly limited, and the method may be defined as the impregnation of the support using a metallic raw material. For example, an impregnation method, an ion exchange method, or a co-precipitation method may be used.

In the preset invention, a step of reducing the terephthalic acid may be performed in the presence of the first metal catalyst, and may include a step of reducing a reduction product of the terephthalic acid in the presence of the second metal catalyst. In this case, the second metal catalyst may include the ruthenium (Ru) compound, the tin (Sn) compound, and the platinum (Pt) compound in a weight ratio of 1:0.8 to 1.2:0.2 to 0.6.

That is, the present inventors conducted research into a method of synthesizing a cycloalkane diol by direct hydrogenation of aromatic dicarboxylic acid and confirmed, through experimentations, that, when the first metal catalyst and the second metal catalyst are used, the aromatic dicarboxylic acid may be reduced with high efficiency without a decrease in reactivity due to the long-term use.

Specifically, terephthalic acid is reduced using the first metal catalyst, and, when the reduction product of the terephthalic acid is then again reduced using the second metal catalyst including the ruthenium (Ru) compound, the tin (Sn) compound, and the platinum (Pt) compound in a specific weight ratio, almost all of the terephthalic acid, as a reactant, participate in the reaction to achieve a high conversion rate and high purity 1,4-cyclohexanedimethanol may be prepared in a shorter period of time while minimizing by-products.

According to such a method of preparing 1,4-cyclohexanedimethanol, since the generation of by-products is insignificant in a process of synthesizing 1,4-cyclohexanedimethanol from terephthalic acid, an additional process or step for separating and recovering the by-products may be omitted and a refining process for increasing purity may be minimized. Also, since a relatively simplified reaction process design is possible and high purity 1,4-cyclohexanedimethanol may be prepared in a high yield in a shorter period of time, the efficiency and economic efficiency of the entire preparation process may be improved.

As described above, the method of preparing 1,4-cyclohexanedimethanol according to the present invention may include a step of reducing terephthalic acid in the presence of a first metal catalyst including a palladium (Pd) compound.

A benzene ring of the terephthalic acid may be reduced by the first metal catalyst including a palladium (Pd) compound, and accordingly, 1,4-cyclohexanedicarboxylic acid may be formed.

The first metal catalyst may include a palladium (Pd) compound to be fixed to the support, and may include 0.05 wt % to wt %, for example, 0.1 wt % to 5 wt %, of palladium and a remaining amount of the support. In this case, the palladium (Pd) compound denotes a palladium metal itself, an organic salt of palladium, or an inorganic salt of palladium.

Various reduction methods may be used in the step of reducing terephthalic acid, and, for example, a step of contacting the terephthalic acid and hydrogen gas may be included. Also, in the step of reducing terephthalic acid, a method, reaction conditions, and an apparatus, which are known to be used in a reduction reaction of aromatic carboxylic acid, may be used without particular limitation, and, for example, the method may be performed at a temperature of 50° C. to 350° C., for example, 100° C. to 300° C. and a pressure of 30 bar to 150 bar, for example, 40 bar to 100 bar.

Specifically, the step of reducing terephthalic acid may be performed by including a step of introducing hydrogen gas and increasing an internal temperature after converting the inside of the reactor, in which the first metal catalyst including a palladium (Pd) compound and the terephthalic acid are present, to an atmosphere of inert gas such as nitrogen.

In the step of reducing terephthalic acid, the first metal catalyst may be used in an amount of 1 part by weight to 50 parts by weight, for example, 3 parts by weight to 40 parts by weight, based on 100 parts by weight of the terephthalic acid. When the amount or the used amount of the first metal catalyst based on the terephthalic acid is excessively small, the efficiency of the reduction reaction may be reduced or the selectivity of the 1,4-cyclohexanedimethanol in the finally prepared reaction product may be reduced, and, when the amount of the catalyst is less than the above range, production efficiency of a reaction apparatus may be reduced and the efficiency of the apparatus may be reduced or energy consumption may be excessive when separation and recovery are performed after the final product is obtained. Also, when the amount or the used amount of the first metal catalyst based on the terephthalic acid is excessively large, since excessive amounts of by-products are generated in the reaction process, a multi-step process must be additionally performed to remove the by-products. Thus, it is uneconomical and purity of the finally prepared product may be reduced.

The method of preparing 1,4-cyclohexanedimethanol according to the present invention may include a step of reducing the reduction product of the terephthalic acid, which is obtained through the step of reducing terephthalic acid, in the presence of a second metal catalyst including a ruthenium (Ru) compound, a tin (Sn) compound, and a platinum (Pt) compound in a weight ratio of 1:0.8 to 1.2:0.2 to 0.6, for example, 1:0.9 to 1.1:0.3 to 0.55.

Ruthenium included in the second metal catalyst seems to convert dicarboxylic acid to primary alcohol, tin seems to increase the selectivity of the alcohol as a synthesis product, and platinum seems to suppress a side reaction by increasing activity of the catalyst.

When the reduction product of the terephthalic acid including 1,4-cyclohexanedicarboxylic acid is reduced in the presence of the second metal catalyst, a reaction product including 1,4-cyclohexanedimethanol may be formed.

As confirmed in examples to be described later, since the second metal catalyst including the ruthenium (Ru) compound, the tin (Sn) compound, and the platinum (Pt) compound in the specific weight ratio is used to participate almost all of the terephthalic acid used as the reactant in the reaction, a high conversion rate may be achieved and the selectivity of the 1,4-cyclohexanedimethanol in the finally prepared reaction product may be highly maintained.

Herein, the ruthenium (Ru) compound denotes a ruthenium metal itself, an organic salt of ruthenium, or an inorganic salt of ruthenium. The same applies to the tin (Sn) compound and the platinum (Pt) compound.

The second metal catalyst may include a ruthenium (Ru) compound, a tin (Sn) compound, and a platinum (Pt) compound which are fixed to the support. In this case, the second metal catalyst may include 0.5 wt % to 20 wt %, particularly 1 wt % to 15 wt %, and more particularly 5 wt % to 12 wt % of the ruthenium (Ru) compound, and amounts of the tin (Sn) compound and the platinum (Pt) compound in the second metal catalyst may be determined by the amount of the ruthenium compound and a weight ratio between the metal compounds.

When the amounts of the ruthenium (Ru) compound, tin (Sn) compound, and platinum (Pt) compound in the second metal catalyst are excessively small, the efficiency of the reduction reaction may be reduced or the selectivity of the 1,4-cyclohexanedimethanol in the finally prepared reaction product may be reduced, a reaction yield may be reduced due to the generation of unreacted carboxylic acid or carboxylic anhydride, and the efficiency may be reduced or energy consumption may be excessive when the final reaction product is separated or recovered. Also, when the amounts of the ruthenium (Ru) compound, tin (Sn) compound, and platinum (Pt) compound in the second metal catalyst are excessively large, since additional reactions excessively occur, a primary alcohol type, hydrolysis thereof, or alkane equivalent thereto may be formed to reduce the reaction yield or reduce the purity of the final reaction product. Since a multi-step process must be additionally performed to remove the generated by-products, economic efficiency of the process may also be reduced.

Various reduction methods may be used in the step of reducing the reduction product of the terephthalic acid, and, for example, a step of contacting the reduction product of the terephthalic acid and hydrogen gas may be included. Also, in the step of reducing the reduction product of the terephthalic acid, a method, reaction conditions, and an apparatus, which are known to be used in a reduction reaction of aromatic carboxylic acid, may be used without particular limitation, and, for example, the method may be performed at a temperature of 50° C. to 350° C., for example, 100° C. to 300° C. and a pressure of 30 bar to 150 bar, for example, 40 bar to 100 bar.

Specifically, the step of reducing the reduction product of the terephthalic acid may be performed by including a step of introducing hydrogen gas and increasing an internal temperature after converting the inside of the reactor, in which the second metal catalyst and the reduction product of the terephthalic acid are present, to an atmosphere of inert gas such as nitrogen.

In the step of reducing the reduction product of the terephthalic acid, the second metal catalyst may be used in an amount of 1 part by weight to 50 parts by weight, for example, 3 parts by weight to 40 parts by weight, based on 100 parts by weight of the reduction product of the terephthalic acid. When the amount or the used amount of the second metal catalyst based on the reduction product of the terephthalic acid is excessively small, the efficiency of the reduction reaction may be reduced or the selectivity of the 1,4-cyclohexanedimethanol in the finally prepared reaction product may be reduced, and, when the amount of the catalyst is less than the above range, the production efficiency of the reaction apparatus may be reduced and the efficiency of the apparatus may be reduced or energy consumption may be excessive when separation and recovery are performed after the final product is obtained. Also, when the amount or the used amount of the second metal catalyst based on the reduction product of the terephthalic acid is excessively large, since excessive amounts of by-products are generated in the reaction process, a multi-step process must be additionally performed to remove the by-products. Thus, it is uneconomical and purity of the finally prepared reaction product may be reduced.

As described above, a typically known support may be used as the support, which may be included in the first metal catalyst or the second metal catalyst, without particular limitation, and, for example, a metal oxide, such as silica, alumina, zirconium oxide, and titanium dioxide, a composite oxide, such as silica-alumina, acidic activated carbon, and zeolite may be used.

Herein, an active component of each of the first metal catalyst and the second metal catalyst may be used in a state of being fixed to a zeolite support, wherein, since the active component is fixed to the zeolite support, results may be obtained in which 90% or more of the selectivity of the 1,4-cyclohexanedimethanol is secured in the finally prepared product while securing a high reaction conversion rate of 99% or more. Such an effect may be due to a ratio of alumina to silica and acidity of the zeolite support and an effect of smooth reaction according to an appropriate pore size.

Specifically, the zeolite support included in each of the first metal catalyst and the second metal catalyst may have a specific surface area of 200 m$^2$/g to 900 m$^2$/g, for example, 300 m$^2$/g to 800 m$^2$/g. When the specific surface area of the zeolite support is excessively small, since active sites of the reactant and catalyst are reduced, the reaction may not be smoothly performed, or since a metal, which plays an important role in the catalyst, is not properly impregnated in the support, a phenomenon may occur in which pores are clogged or broken. Also, when the specific surface area of the zeolite support is excessively large, since a degree of dispersion of the catalyst metal is excessively increased, the reaction may not be smoothly performed.

A total pore volume of the zeolite support included in each of the first metal catalyst and the second metal catalyst may be 1.2 cm$^3$/g or less. When the total pore volume of the zeolite support included in each of the first metal catalyst and the second metal catalyst is excessively large, since a reaction rate between the reactant and the catalyst is excessively high, excessive amounts of by-products are generated or the metal, as the active component, is not sufficiently dispersed. Accordingly, since contact efficiency of the reactant and the catalyst is significantly reduced, the reaction may not be smoothly performed.

Furthermore, in the zeolite support included in each of the first metal catalyst and the second metal catalyst, a volume of pores having a radius of 10 Å or less may be in a range of 0.1 cm$^3$/g to 0.8 cm$^3$/g, for example, 0.2 cm$^3$/g to 0.7 cm$^3$/g. The pores having a radius of 10 Å or less in the zeolite support included in each of the first metal catalyst and the second metal catalyst may function to increase enantioselectivity as well as activity. When the volume of the pores having a radius of 10 Å or less in the zeolite support is excessively small, since organic macromolecules may not be adsorbed to the micropores, a pore structure may not only be destroyed by pressure during the subsequent molding of the catalyst or a high heat treatment during sintering, but an internal surface area of the pores may also be rapidly reduced to lose material adsorption characteristics and, in addition, metal catalyst components may be discharged. Also, when the volume of the pores having a radius of 10 Å or less in the zeolite support is excessively large, since the reaction rate is accelerated while the degree of dispersion of the metal catalyst is increased, excessive amounts of by-products may be generated or selectivity of enantiomers of the product may be reduced.

The zeolite support included in each of the first metal catalyst and the second metal catalyst may be Y-type zeolite, a case, in which each active component is fixed to the zeolite support, may secure a higher selectivity of the 1,4-cyclohexanedimethanol in comparison to a case in which other types of supports, for example, a support, such as activated carbon, are used, and the activity may be increased or thermal, mechanical, and reaction stability may be obtained during catalyst molding.

In each of the step of reducing terephthalic acid and the step of reducing the reduction product of the terephthalic acid, the reactant itself may be subjected to a direct reduction reaction, and a reduction reaction may occur in a state in which the reactant is present in a solvent.

Examples of the usable solvent are not particularly limited, and, for example, water or an organic solvent may be used. As an example of the organic solvent, aliphatic alcohols, such as methanol, ethanol, propanol, and cyclohexanol, aliphatic hydrocarbons, such as hexane and cyclohexane, ethers, such as diethyl ether and tetrahydrofuran, or a mixture of two or more thereof may be used. An amount of the organic solvent used is not particularly limited, and, for example, the organic solvent may be used in an amount of 10% to 1,000% based on a weight of the terephthalic acid as the reactant and/or the reduction product of the terephthalic acid.

The preparation of the 1,4-cyclohexanedimethanol may further include a step of refining the reaction product after the used catalyst is separated at the time of the completion of each reduction reaction process. A method, which may be used in the refinement, is not particularly limited, but the separation and refinement may be performed according to a distillation method, an extraction method, and a chromatographic method.

In the method of preparing 1,4-cyclohexanedimethanol according to the present invention, the step of reducing terephthalic acid and the step of reducing the reduction product of the terephthalic acid may be continuously performed. Herein, the expression "continuously performed" denotes that 1,4-cyclohexanedimethanol may be formed from terephthalic acid through a single process or reaction process.

Also, the step of reducing terephthalic acid and the step of reducing the reduction product of the terephthalic acid may be performed in a single reactor. Herein, the expression "performed in a single reactor" denotes that the reduction of the terephthalic acid and the secondary reduction of the reduction product of the terephthalic acid are performed in the same reactor without the separation into separate processes or the transfer of the reaction product.

In the present invention, it was found that, using a reactor in which the first metal catalyst and the second metal catalyst are separately and sequentially injected into a fixed bed, the process is simplified so that the twice reduction are continuously performed under the same process condition of the unified catalytic fixed bed in the same reactor, and thus, a molar ratio of trans-1,4-cyclohexanedimethanol in the finally prepared 1,4-cyclohexanedimethanol may be obtained at a level of 20% while dramatically reducing the process time.

Also, as an apparatus for preparing 1,4-cyclohexanedimethanol which may realize the preparation method, disclosed is an apparatus for preparing 1,4-cyclohexanedimethanol which includes a reactor including a raw material feeding unit, in which terephthalic acid is transferred and introduced into a top end, a reaction section, in which a reduction reaction of the terephthalic acid introduced from the raw material feeding unit is performed, and an outlet which is formed at a bottom end to allow a product generated in the reaction section to be transferred to a receiver; a preheater in which the terephthalic acid and ion exchange water are introduced to transfer dissolved terephthalic acid to the reactor by an inert gas through a mass flow controller; and the receiver which recovers the product from the outlet from which the product generated in the reaction section is discharged, wherein the reaction section includes an upper reaction section, in which a first metal catalyst including a palladium (Pd) compound is injected to perform a reduction reaction of the terephthalic acid introduced from the raw material feeding unit, and a lower reaction section in which a second metal catalyst, as a catalyst including a ruthenium (Ru) compound, a tin (Sn) compound, and a platinum (Pt) compound in a weight ratio of 1:0.8 to 1.2:0.2 to 0.6, is injected to form an interface with the first metal catalyst and perform a reduction reaction of a resultant product reduced in the upper reaction section.

FIG. 1 is a schematic view illustrating an apparatus, which prepares trans-1,4-cyclohexanedimethanol by reducing terephthalic acid, according to an embodiment of the present invention.

Referring to FIG. 1, an apparatus 100, which prepares 1,4-cyclohexanedimethanol by performing a continuous reduction reaction by hydrogenation according to the present invention, may include a reactor 110, a preheater 120 in which a pretreatment process is performed during the input of a terephthalic acid raw material, nitrogen gas and hydrogen gas input devices, and a receiver 130.

The inside of the reactor 110, in which continuous reduction including hydrogenation of terephthalic acid is performed in the present invention, is in a state in which a first metal catalyst and a second metal catalyst are sequentially injected into a fixed bed. The hydrogenation is performed by including a step of mixing the terephthalic acid with water, and a first reaction, which reduces using the first metal catalyst through a catalytic fixed bed 111 initially injected into the reactor 110, and a second reaction, which reduces using the second metal catalyst, are continuously performed to obtain trans-1,4-cyclohexanedimethanol as the final product. The reactor 110 is composed of an acid-resistant container, and a terephthalic acid-containing solution passes through the catalyst in a state in which the first metal catalyst and the second metal catalyst are sequentially impregnated in the fixed bed 111 while flowing with hydrogen gas in the reactor 110.

The acid-resistant container used in the present invention may include a metallic material having high acid resistance, such as Hastelloy, Inconel, or molded articles thereof, and a material having high acid resistance other than metal, for example, glassy materials, such as ceramic, enamel, and glass, or molded articles thereof, but, since stainless steel or Hastelloy, which is typically used in a pressure-resistant container, is more acid resistant and economically efficient, economical hydrogenation may be realized while suppressing the reduction of catalytic activity.

After the terephthalic acid and ion exchange water are introduced and nitrogen is injected, the preheater 120 may be installed to increase the solubility in water under conditions including a temperature of 250° C. to 300° C., for example, 270° C. to 290° C., and a pressure of 60 kg/cm$^2$ to 100 kg/cm$^2$, for example, 70 kg/cm$^2$ to 90 kg/cm$^2$. In this case, a concentration of the terephthalic acid may be in a range of 1 wt % to 100 wt %, for example, 5 wt % to 50 wt %. The reason for this is that, in a case in which the concentration of the terephthalic acid is less than wt %, since a concentration of the trans-1,4-cyclohexanedimethanol is low, it may be difficult to obtain trans-1,4-cyclohexanedimethanol, and, in a case in which the concentration of the terephthalic acid is greater than 50 wt %, it may be difficult to adjust process operating conditions due to physical property characteristics of the trans-1,4-cyclohexanedimethanol.

When the nitrogen gas is transferred to the reactor through a mass flow controller (MFC) 140, a rate of 0 sccm to 50 sccm is appropriate, and the rate may be adjusted to a range of 10 sccm to 50 sccm, for example, 20 sccm to 40 sccm. In a case in which the operation is performed at a rate of less than 10 sccm, since pressure is insufficient when the terephthalic acid mixture is transferred from the preheater 120 to the reactor 110, it may be difficult to transfer the terephthalic acid mixture, and, in a case in which the operation is performed at a rate of greater than 50 sccm, since the transfer of the reaction mixture from the preheater 120 to the reactor 110 is rapidly performed to clog an intermediate line 150, the transfer of the reaction mixture may be difficult.

Also, hydrogen gas through a mass flow controller (MFC) 160 meets the nitrogen gas containing a terephthalic acid mixed solution in the intermediate line 150 to be moved to an inlet of the reactor and simultaneously, synthesis of the trans-1,4-cyclohexanedimethanol through first metal catalyst and second metal catalyst reactions may be sequentially performed. In this case, the movement of the hydrogen gas may be controlled at a rate of 100 sccm to 5,000 sccm, for example, 1,000 sccm to 4,000 sccm. When the movement of the hydrogen gas through the mass flow controller 160 is not properly performed, since the reaction between the reactant transferred to the reactor 110 and the metal catalyst is not smoothly performed, excessive amounts of by-products are generated, and thus, there is a need to control the hydrogen gas at an appropriate flow rate. In particular, since the reaction is performed in the single reactor 110, the primary reduction of the terephthalic acid and the secondary reduction are performed without the separation into separate processes or the transfer of the reaction product, and thus, the appropriate hydrogen gas flow rate may affect the generation of the trans-1, 4-cyclohexanedimethanol.

The inside of the reactor 110, in which the reduction reaction of the terephthalic acid is performed, may be maintained at a temperature of 50° C. to 350° C., for example, 100° C. to 300° C. and a pressure of 30 bar to 150 bar, for example, 40 bar to 100 bar, and the same applies to the continuous reduction reaction. When the reaction is performed under conditions of lower or higher temperatures and pressures, since excessive amounts of by-products are generated to additionally require a refining process, it is uneconomical and subsequently, it may adversely affect the purity of the resultant product.

The reactor 110 in the present invention is a jacket-type, wherein the reactor 110 may be composed of a raw material feeding unit 112, in which the terephthalic acid dissolved by the preheater 120 is transferred and introduced into the top end, a reaction section 111, in which the reduction reaction of the terephthalic acid introduced from the raw material feeding unit 112 is performed, and an outlet 113 which is formed at the bottom end to allow the product generated in the reaction section 111 to be transferred to the receiver 130.

The reaction section 111 is composed of a catalytic fixed bed to allow the first metal catalyst and the second metal catalyst to be present sequentially, wherein the reaction section 111 may include an upper reaction section 111a, in which the first metal catalyst including a palladium (Pd) compound is injected to perform the reduction reaction of the terephthalic acid introduced from the raw material feeding unit 112, and a lower reaction section 111b in which the second metal catalyst, as a catalyst including a ruthenium (Ru) compound, a tin (Sn) compound, and a platinum (Pt) compound, is injected to form an interface F with the first metal catalyst and perform the reduction reaction of the resultant product reduced in the upper reaction section 111a.

Specifically, after the terephthalic acid is reduced by the first metal catalyst of the upper reaction section 111a, since almost all of the terephthalic acid, as the reactant, participate in the reaction while the reduced product is again reduced by the second metal catalyst including the ruthenium (Ru) compound, the tin (Sn) compound, and the platinum (Pt) compound in a specific weight ratio immediately after the reduced product passes through the interface F to enter into the lower reaction section 111b, a high conversion rate may be achieved and high purity 1,4-cyclohexanedimethanol may be obtained in a shorter period of time while minimizing by-products.

Various reducing methods may be used in the process of reducing the reduced product of the terephthalic acid, and, for example, the method may be performed by a process of contacting the reduced product of the terephthalic acid and hydrogen gas. In the process, a method, reaction conditions, and an apparatus, which are known to be used in a reduction reaction of aromatic carboxylic acid, may be used without particular limitation, and, for example, the method may be performed under the same process condition as that of the upper reaction section 111a, i.e., at a temperature of 50° C. to 350° C., for example, 100° C. to 300° C. and a pressure of 30 bar to 150 bar, for example, 40 bar to 100 bar. Specifically, the process of reducing the reduced product of the terephthalic acid may be performed in a state in which conversion into an atmosphere of inert gas such as nitrogen, introduction of hydrogen gas, and an increase in the internal temperature are already performed in the lower reaction section 111b in which the second metal catalyst and the reduced product of the terephthalic acid are present.

In the process of reducing the reduced product of the terephthalic acid, the second metal catalyst may be allowed to be injected into the catalytic fixed bed 111 of the lower reaction section 111b in advance so that the second metal catalyst is included in an amount of 1 part by weight to 50 parts by weight, for example, 3 parts by weight to 40 parts by weight, based on the support catalyst in which active metal is loaded in an amount of 5 wt % to 10 wt % based on 100 parts by weight of the terephthalic acid.

Hereinafter, exemplary embodiments of the present invention will be described in detail to fully explain the present invention in such a manner that it may easily be carried out by a person with ordinary skill in the art to which the present invention pertains. However, the following examples are merely presented to exemplify the present invention, and the present invention is not limited to the exemplary embodiments set forth herein.

Example 1: Direct Conversion Reaction of Terephthalic Acid to 1,4-Cyclohexanedimethanol Using Activated Carbon Supported Catalyst Preparation Example 1-1: Preparation of First Metal Catalyst 10 g of activated carbon (Aldrich) and a 60% nitric acid aqueous solution were charged into a 500 ml beaker and the mixture was then stirred after the temperature was increased to 80° C. After the completion of the stirring, the activated carbon was washed using ion exchange water and dried under reduced pressure. The activated carbon and palladium chloride were dissolved in a hydrochloric acid aqueous solution in a 500 ml beaker, and water was then removed by evaporation to obtain a residue. The obtained residue was dried under reduced pressure and then sintered at a temperature of 300° C. for 3 hours in an atmospheric pressure to prepare a first metal catalyst containing activated carbon impregnated with 0.5 wt % of palladium.

Preparation Example 1-2: Preparation of Second Metal Catalyst 10 g of activated carbon (Aldrich) and a 60% nitric acid aqueous solution were charged into a 500 ml beaker and the mixture was then stirred after the temperature was increased to 80° C. After the completion of the stirring, the activated carbon was washed using ion exchange water and dried under reduced pressure. Ruthenium chloride trihydrate, tin chloride dihydrate, and chloroplatinic acid were dissolved with the activated carbon in a hydrochloric acid aqueous solution in a 500 ml beaker, and water was then removed by evaporation to obtain a residue. The obtained residue was dried under reduced pressure and then sintered at a temperature of 300° C. for 3 hours in an atmospheric pressure to prepare a second metal catalyst in which ruthenium (Ru), tin (Sn), and platinum (Pt) were loaded onto the activated carbon. A weight ratio of ruthenium (Ru), tin (Sn), and platinum (Pt) was as described in the following Table 1.

Preparation Example 1-3: Preparation of Second Metal Catalyst

A second metal catalyst was prepared in the same manner as in Preparation Example 1-2 except that Y-zeolite was used instead of the activated carbon in Preparation Example 1-2.

Preparation Example 1-4: Preparation of Metal Catalyst

A metal catalyst was prepared in the same manner as in Preparation Example 1-2 except that ruthenium chloride trihydrate and chloroplatinic acid were only dissolved in a hydrochloric acid aqueous solution without tin chloride dihydrate in Preparation Example 1-2.

Example 1-1

3.0 g of the first metal catalyst obtained in Preparation Example 1-1, 10.0 g of terephthalic acid, and 100 g of ion exchange water were charged into a 300 ml high-pressure reactor equipped with a stirrer. An atmosphere in the high-pressure reactor was replaced with nitrogen at room temperature and a temperature in the high-pressure reactor was then increased to 230° C. to perform hydrogenation while hydrogen gas was introduced into the high-pressure reactor at a rate of 28 kg/cm². In this case, a stirring speed in the high-pressure reactor was fixed to 450 rpm and the reaction was performed until there was no change in internal pressure. After the inside of the reactor was cooled to room temperature in a state in which there was no change in the internal pressure of the high-pressure reactor, 3.0 g of the second metal catalyst obtained in Preparation Example 1-2 was added and an atmosphere in the reactor was replaced with nitrogen. Thereafter, hydrogen gas was injected into the reactor at a rate of 50 kg/cm² and the temperature in the high-pressure reactor was increased to 230° C. to perform hydrogenation. The stirring speed in the high-pressure reactor was fixed to 450 rpm and the reaction was performed until there was no change in the internal pressure. At a time when there was no change in the internal pressure, the inside of the reactor was cooled to 70° C. and the reactor was dismantled to collect a reaction product. Water was removed from the collected reaction product by distillation at 45° C. using a rotary evaporator to obtain 1,4-cyclohexanedimethanol as a final product. Thereafter, a conversion rate of the reactant (terephthalic acid) and selectivity of the 1,4-cyclohexanedimethanol were measure for the obtained final product using gas chromatography (GC).

Specifically, the reaction product was diluted with methanol so that a concentration of the 1,4-cyclohexanedimethanol in the reaction product obtained by the reduction reaction (hydrogenation) of the reactant (terephthalic acid) became about 1 wt %. Gas chromatography was performed on the diluted solution under the following conditions to calculate the selectivity of the 1,4-cyclohexanedimethanol, and, after converting each value to a molar ratio (%), the selectivity was calculated by an equation, [(1,4-cyclohexanedimethanol/product)×100]. With respect to the terephthalic acid, since solubility in water was not good, the conversion rate and selectivity were calculated using the terephthalic acid remained after the reaction and a filtrate remained after the filtration of the catalyst.

[Gas Chromatography Conditions]
1) Column: Agilent 19091J (column length 30 m, internal diameter 0.32 mm, film thickness 0.25 μm)
2) GC System: Gas Chromatography, Model Agilent 7890
3) Carrier Gas: Helium
4) Detector: Flame Ionization Detector (FID)

Example 1-2

1,4-cyclohexanedimethanol was prepared in the same manner as in Example 1-1 except that the second metal catalyst obtained in Preparation Example 1-3 was used in Example 1-1.

Examples 1-3 to 1-5

1,4-cyclohexanedimethanols were prepared in the same manner as in Example 1-1 except that second metal catalysts having weight ratios of ruthenium (Ru), tin (Sn), and platinum (Pt) listed in the following Table 1 were used in Example 1-1.

Example 1-6

1,4-cyclohexanedimethanol was prepared in the same manner as in Example 1-1 except that, in Example 1-1, 3.0 g of the second metal catalyst was added, an atmosphere in the reactor was replaced with nitrogen, hydrogen gas was injected into the reactor at a rate of 50 kg/cm², the temperature in the high-pressure reactor was increased to 230° C., and the internal pressure was set to 50 bar to perform hydrogenation.

Comparative Example 1-1

3.0 g of the first metal catalyst obtained in Preparation Example 1-1, 3.0 g of the second metal catalyst obtained in Preparation Example 1-2, 10.0 g of terephthalic acid, and 100 g of ion exchange water were charged into a 300 ml high-pressure reactor equipped with a stirrer. An atmosphere in the high-pressure reactor was replaced with nitrogen at room temperature and a temperature in the high-pressure reactor was then increased to 230° C. to perform hydrogenation while hydrogen gas was introduced into the high-pressure reactor at a rate of 50 kg/cm². In this case, a stirring speed in the high-pressure reactor was fixed to 450 rpm and the reaction was performed until there was no change in internal pressure. At a time when there was no change in the internal pressure, the inside of the reactor was cooled to room temperature and the reactor was dismantled to collect a reaction product. Water was removed from the collected reaction product by distillation at 45° C. using a rotary evaporator to obtain 1,4-cyclohexanedimethanol as a final product. Thereafter, a conversion rate of the reactant (terephthalic acid) and selectivity of the 1,4-cyclohexanedimethanol were measure for the obtained final product using gas chromatography (GC).

Comparative Example 1-2

1,4-cyclohexanedimethanol was prepared in the same manner as in Comparative Example 1-1 except that 3.0 g of the first metal catalyst obtained in Preparation Example 1-1 was not used in Comparative Example 1-1.

Comparative Example 1-3

1,4-cyclohexanedimethanol was prepared in the same manner as in Comparative Example 1-1 except that 3.0 g of the second metal catalyst obtained in Preparation Example 1-2 was not used in Comparative Example 1-1.

Comparative Example 1-4

1,4-cyclohexanedimethanol was prepared in the same manner as in Comparative Example 1-1 except that 3.0 g of the metal catalyst obtained in Preparation Example 1-4 was used instead of the second metal catalyst in Comparative Example 1-1.

The catalysts used in Examples 1-1 to 1-6 and Comparative Examples 1-1 to 1-4, reaction conditions, and reaction results (conversion rate of terephthalic acid, selectivity of 1,4-cyclohexanedimethanol) are listed in the following Table 1.

TABLE 1

| Category | Catalyst used | Second metal catalyst composition [wt % in supported catalyst] (Ru:Sn:Pt) | Reaction conditions Temperature (° C.) | Pressure (bar) | Results (GC, %) Conversion rate | Selectivity |
|---|---|---|---|---|---|---|
| Example 1-1 | 1)Pd/C 2)Ru—Sn—Pt/C | 10:10:4 | 230 | 80 | 100 | 85 |
| Example 1-2 | 1)Pd/C 2)Ru—Sn—Pt/Zeolite | 10:10:4 | | | 100 | 78 |
| Example 1-3 | 1)Pd/C 2)Ru—Sn—Pt/C | 5:5:2 | | | 100 | 77 |
| Example 1-4 | 1)Pd/C 2)Ru—Sn—Pt/C | 3:3:1 | | | 100 | 56 |
| Example 1-5 | 1)Pd/C 2)Ru—Sn—Pt/C | 1:1:0.5 | | | 100 | 43 |
| Example 1-6 | 1)Pd/C 2)Ru—Sn—Pt/C | 10:10:4 | | 50 | 100 | 65 |
| Comparative Example 1-1 | Pd/C + Ru—Sn—Pt/C | 10:10:4 | | 80 | 43 | none |
| Comparative Example 1-2 | Ru—Sn—Pt/C | 10:10:4 | | | 53 | none |
| Comparative Example 1-3 | Pd/C | — | | | 77 | none |
| Comparative Example 1-4 | Pd/C + Ru—Pt/C | 10:0:4 | | | 41 | none |

As illustrated in Table 1, in Examples 1-1 to 1-6, it was confirmed that 100% of the terephthalic acid, as the reactant, was converted, and the selectivity of the 1,4-cyclohexanedimethanol in the generated product was 56% or more, particularly 65% or more, and more particularly 77% or more. In contrast, in Comparative Examples 1-1 to 1-4, it was confirmed that the conversion rate was significantly reduced and other by-products, different from 1,4-cyclohexanedimethanol, was generated as the finally prepared product.

Example 2: Direct Conversion Reaction of Terephthalic Acid to 1,4-Cyclohexanedimethanol Using Zeolite Supported Catalyst Preparation Example 2-1: Preparation of First Metal Catalyst A first metal catalyst was prepared by using a conventional incipient wetness method. Specifically, palladium chloride was dissolved in ion exchange water and the solution was then added dropwise to an evaporating dish containing Y-zeolite (specific surface area: about 600 m²/g, total pore volume: 1.0 cm³/g, volume of pores having a radius of 10 Å or less: about 0.5 cm³/g). When the pores of the zeolite were filled with the solution, water was removed by evaporation and a residue was obtained. The obtained residue was dried under reduced pressure and then sintered at a temperature of 550° C. for 3 hours in an atmospheric pressure to prepare a first metal catalyst containing Y-zeolite impregnated with 2.5 wt % of palladium.

Preparation Example 2-2: Preparation of Second Metal Catalyst

A second metal catalyst was also prepared by using an incipient wetness method. Specifically, ruthenium chloride trihydrate was dissolved in ion exchange water and the solution was then added dropwise to an evaporating dish containing Y-zeolite (specific surface area: about 600 m²/g, total pore volume: 1.0 cm³/g, volume of pores having a radius of 10 Å or less: about 0.5 cm³/g). When the pores of the zeolite were filled with the solution, water was removed by evaporation and a residue was obtained. The method performed using the ruthenium chloride trihydrate was repeated for tin chloride dihydrate and chloroplatinic acid, respectively. The obtained residue was dried under reduced pressure and then sintered at a temperature of 550° C. for 3 hours in an atmospheric pressure to prepare a second metal catalyst in which Y-zeolite was impregnated with ruthenium (Ru), tin (Sn), and platinum (Pt). A weight ratio of ruthenium (Ru), tin (Sn), and platinum (Pt) was as described in the following Table 2.

Preparation Example 2-3: Preparation of Second Metal Catalyst

A second metal catalyst was prepared in the same manner as in Preparation Examples 2-1 and 2-2 except that activated carbon was used instead of the Y-zeolite and sintering was performed at 200° C. for 3 hours in Preparation Examples 2-1 and 2-2, respectively.

Preparation Example 2-4: Preparation of Second Metal Catalyst

A second metal catalyst was prepared in the same manner as in Preparation Examples 2-1 and 2-2 except that ZSM-5 zeolite was used instead of the Y-zeolite in Preparation Examples 2-1 and 2-2, respectively.

Example 2-1

10.0 g of the first metal catalyst obtained in Preparation Example 2-1, 10.0 g of terephthalic acid, and 100 g of ion exchange water were charged into a 300 ml high-pressure reactor equipped with a stirrer. An atmosphere in the high-pressure reactor was replaced with nitrogen at room temperature and a temperature in the high-pressure reactor was then increased to 230° C. to perform hydrogenation while hydrogen gas was introduced into the high-pressure reactor at a rate of 28 kg/cm$^2$. In this case, a stirring speed in the high-pressure reactor was fixed to 450 rpm and the reaction was performed until there was no change in internal pressure. After the inside of the reactor was cooled to room temperature in a state in which there was no change in the internal pressure of the high-pressure reactor, 10.0 g of the second metal catalyst obtained in Preparation Example 2-2 was added and an atmosphere in the reactor was replaced with nitrogen. Thereafter, hydrogen gas was injected into the reactor at a rate of 54 kg/cm$^2$ and the temperature in the high-pressure reactor was increased to 230° C. to perform hydrogenation. The stirring speed in the high-pressure reactor was fixed to 450 rpm and the reaction was performed until there was no change in the internal pressure. At a time when there was no change in the internal pressure, the inside of the reactor was cooled to 70° C. and the reactor was dismantled to collect a reaction product. Water was removed from the collected reaction product by distillation at 50° C. using a rotary evaporator to obtain 1,4-cyclohexanedimethanol as a final product. Thereafter, a conversion rate of the reactant (terephthalic acid) and selectivity of the 1,4-cyclohexanedimethanol were measure for the obtained final product using gas chromatography (GC) in the same manner as in Example 1-1.

Examples 2-2 and 2-3

1,4-cyclohexanedimethanols were prepared in the same manner as in Example 2-1 except that first metal catalysts having weight ratios of palladium (Pd) listed in the following Table 2 were used in Example 2-1.

Example 2-4

1,4-cyclohexanedimethanol was prepared in the same manner as in Example 2-1, and the used metal catalyst was dried by evaporation and the same method was repeated to prepare 1,4-cyclohexanedimethanols.

Example 2-5

1,4-cyclohexanedimethanol was prepared in the same manner as in Example 2-1 except that the second metal catalyst obtained in Preparation Example 2-3 was used in Example 2-1.

Examples 2-6 and 2-7

1,4-cyclohexanedimethanols were prepared in the same manner as in Example 2-1 except that first metal catalysts and second metal catalysts having weight ratios of metals listed in the following Table 2 were used in Example 2-1.

Example 2-8

1,4-cyclohexanedimethanol was prepared in the same manner as in Example 2-5, and the used metal catalyst was dried by evaporation and the same method was repeated to prepare 1,4-cyclohexanedimethanols.

Example 2-9

1,4-cyclohexanedimethanol was prepared in the same manner as in Example 2-1 except that the second metal catalyst obtained in Preparation Example 2-4 was used in Example 2-1.

The catalysts used in Examples 2-1 to 2-9, reaction conditions, and reaction results (conversion rate of terephthalic acid, selectivity of 1,4-cyclohexanedimethanol) are listed in the following Table 2.

TABLE 2

| Category | Catalyst used | Metal catalyst composition [wt % in supported catalyst] | Reaction conditions Temperature (° C.) | Pressure (bar) | Results (GC, %) Conversion rate | Selectivity |
|---|---|---|---|---|---|---|
| Example 2-1 | 1)Pd/Y-Zeolite 2)Ru—Sn—Pt/Y-Zeolite | 1)2.5 2)2.5:2.5:1.5 | 230 | 80 | 100 | 93 |
| Example 2-2 | 1)Pd/Y-Zeolite 2)Ru—Sn—Pt/Y-Zeolite | 1)1.0 2)2.5:2.5:1.5 | | | 100 | 91 |
| Example 2-3 | 1)Pd/Y-Zeolite 2)Ru—Sn—Pt/Y-Zeolite | 1)0.5 2)2.5:2.5:1.5 | | | 100 | 90 |
| Example 2-4 | 1)Pd/Y-Zeolite 2)Ru—Sn—Pt/Y-Zeolite | 1)2.5 2)2.5:2.5:1.5 | | | 100 | $1^{st}$: 93 $2^{nd}$: 87 $3^{rd}$: 94 $4^{th}$: 87 $5^{th}$: 86 $6^{th}$: 90 |
| Example 2-5 | 1)Pd/C 2)Ru—Sn—Pt/C | 1)2.5 2)2.5:2.5:1.5 | | | 100 | 78 |
| Example 2-6 | 1)Pd/C 2)Ru—Sn—Pt/C | 1)5 2)5:5:2 | | | 100 | 65 |
| Example 2-7 | 1)Pd/C 2)Ru—Sn—Pt/C | 1)1 2)1:1:0.5 | | | 100 | 43 |
| Example | 1)Pd/C | 1)5 | | | 100 | $1^{st}$: 78 |

TABLE 2-continued

| Category | Catalyst used | Metal catalyst composition [wt % in supported catalyst] | Reaction conditions Temperature (° C.) | Pressure (bar) | Results (GC, %) Conversion rate | Selectivity |
|---|---|---|---|---|---|---|
| 2-8 | 2)Ru—Sn—Pt/C | 2)5:5:2 | | | | $2^{nd}$: 61<br>$3^{rd}$: 55<br>$4^{th}$: 51<br>$5^{th}$: 42<br>$6^{th}$: 32 |
| Example 2-9 | 1)Pd/ZSM-5<br>2)Ru—Sn—Pt/ZSM-5 | 1)2.5<br>2)2.5:2.5:1.5 | | | 75 | 30 |

As illustrated in Table 2, in Examples 2-1 to 2-4, it was confirmed that 100% of the terephthalic acid, as the reactant, was converted, and the selectivity of the 1,4-cyclohexanedimethanol in the generated product was 90% or more. In contrast, in Examples 2-5 to 2-9, it was confirmed that the selectivity was relatively reduced.

Example 3: Direct Conversion Reaction of Terephthalic Acid to 1,4-Cyclohexanedimethanol Using Reactor in which First Metal Catalyst and Second Metal Catalyst are Separately Injected into Fixed Bed Preparation Example 3-1

The first metal catalyst obtained in Preparation Example 2-1 and the second metal catalyst obtained in Preparation Example 2-2 were used in a jacket-type reactor (2l). A catalytic fixed bed was formed by first injecting 30 g (based on active metal) of the second metal catalyst into a lower reaction section of the reactor and by sequentially injecting 30 g (based on active metal) of the first metal catalyst into an upper reaction section so as to form an interface with the second metal catalyst, and an internal temperature was increased to 280° C. to stably maintain an overall temperature of the reactor. After 100 g of terephthalic acid and 1,000 ml of ion exchange water were introduced into a preheater, nitrogen was charged and the internal temperature was increased to 280° C. to facilitate the dissolution of the terephthalic acid. In this case, stirring was performed to allow the terephthalic acid and ion exchange water to be sufficiently dissolved by fixing a stirring speed in the preheater to 1,000 rpm and being left standing for 2 hours. Nitrogen gas, which will transfer the terephthalic acid dissolved in the ion exchange water from the preheater to the reactor, was maintained at a rate of 30 sccm through a mass flow controller (MFC) to allow the reactant to be sufficiently reacted with the catalyst introduced into the reactor. Also, hydrogen gas introduced for the reduction reaction using a mass flow controller (MFC) was injected at a rate of 3,000 sccm for 4 hours to allow the reactant to be sufficiently reacted with the metal catalysts, wherein, since trans-1,4-cyclohexanedimethanol generated in this case naturally moved to a receiver, a temperature of the receiver was maintained at 80° C. to facilitate the movement of the trans-1,4-cyclohexanedimethanol to the receiver. The hydrogen gas was injected until the terephthalic acid mixture was no longer discharged from the preheater. Thereafter, the inside of the receiver was cooled to 50° C. and the receiver was dismantled to collect a reaction product. Water was removed from the collected reaction product by distillation at 50° C. using a rotary evaporator to obtain trans-1,4-cyclohexanedimethanol as a final product. A conversion rate of the reactant (terephthalic acid) and selectivity of the trans-1,4-cyclohexanedimethanol were measure for the obtained final product using gas chromatography under the same conditions as those of Example 1-1, and the results thereof are presented in the following Table 3.

Example 3-2

Trans-1,4-cyclohexanedimethanol was prepared in the same manner as in Example 3-1 except that the first metal catalyst was adjusted to include palladium in an amount of 1.0 wt % in Example 3-1, and conversion rate and selectivity were then measured. The results thereof are presented in the following Table 3.

Example 3-3

Trans-1,4-cyclohexanedimethanol was prepared in the same manner as in Example 3-1 except that the first metal catalyst was adjusted to include palladium in an amount of 0.5 wt % in Example 3-1, and conversion rate and selectivity were then measured. The results thereof are presented in the following Table 3.

In the following Table 3, the results of Examples 2-1 to 2-3 are presented together for comparison.

TABLE 3

| Category | Conversion rate (%) | Selectivity (%) | Cis:Trans (molar ratio) |
|---|---|---|---|
| Example 3-1 | 100 | 98 | 81:19 |
| Example 3-2 | 100 | 92 | 80:20 |
| Example 3-3 | 100 | 89 | 79:21 |
| Example 2-1 | 100 | 93 | 80:20 |
| Example 2-2 | 100 | 91 | 79:21 |
| Example 2-3 | 100 | 90 | 79:21 |

Referring to Table 3, in a case in which the first metal catalyst including a palladium (pd) compound and the second metal catalyst including a ruthenium (Ru) compound, a tin (Sn) compound, and a platinum (Pt) compound at an optimal weight ratio were first used as in Examples 2-1 to 2-3, the reactor was stopped after the reduction of the terephthalic acid, and the reduction product was again reduced by setting process conditions again, it may be understood that a conversion rate of 100% and a selectivity of 90% or more were obtained, and a molar ratio of cis:trans of the 1,4-cyclohexanedimethanol was good at a level of 80:20.

Also, in a case in which the process is simplified so that the reduction of the terephthalic acid and the reduction of the reduction product of the terephthalic acid were continuously performed under the same process conditions of the unified catalytic fixed bed in the same reactor by introducing the terephthalic acid into the reactor in which the first metal catalyst including a palladium (Pd) compound and the second metal catalyst including a ruthenium (Ru) compound, a tin (Sn) compound, and a platinum (Pt) compound at an optimal content ratio were separately and sequentially injected into the fixed bed, a conversion rate of 100% and a selectivity of 98% were obtained, and a molar ratio of cis:trans of the 1,4-cyclohexanedimethanol was obtained at a level of 80:20. Thus, it may be confirmed that economic efficiency of the preparation process was not only obtained through the simplification of the design of the reactor, but Examples 3-1 to 3-3 also had an equivalent or higher efficiency in comparison to Examples 2-1 to 2-3.

Although preferred embodiments of the present invention have been described in detail, it will be understood by those of ordinary skill in the art that various changes in form and details may be made therein without departing from the spirit and scope of the invention as defined by the following claims.

Thus, the scope of the invention is defined by the following claims rather than the foregoing detailed description, and it is to be interpreted that all changes or modifications derived from the meaning, scope and equivalent concept of the appended claims are within the scope of the present invention.

The invention claimed is:

1. A composite metal catalyst composition which converts an aromatic dicarboxylic acid to an alicyclic diol compound by comprising a first metal catalyst including a palladium (Pd) compound; and a second metal catalyst including a ruthenium (Ru) compound, a tin (Sn) compound, and a platinum (Pt) compound.

2. A method of preparing 1,4-cyclohexanedimethanol, the method comprising reducing terephthalic acid in the presence of a composite metal catalyst composition which comprises a first metal catalyst including a palladium (Pd) compound; and a second metal catalyst including a ruthenium (Ru) compound, a tin (Sn) compound, and a platinum (Pt) compound.

3. The method of claim 2, wherein the reducing of the terephthalic acid is performed in the presence of the first metal catalyst, and comprises reducing a reduction product of the terephthalic acid in the presence of the second metal catalyst.

4. The method of claim 3, wherein the second metal catalyst comprises the ruthenium (Ru) compound, the tin (Sn) compound, and the platinum (Pt) compound in a weight ratio of 1:0.8 to 1.2:0.2 to 0.6.

5. The method of claim 4, wherein the reducing of the terephthalic acid and the reducing of the reduction product of the terephthalic acid are continuously performed.

6. The method of claim 5, wherein the reducing of the terephthalic acid and the reducing of the reduction product of the terephthalic acid are performed in a single reactor.

7. The method of claim 6, wherein, in the reactor, the first metal catalyst and the second metal catalyst are separately and sequentially injected into a fixed bed.

8. The method of claim 2, wherein each of the first metal catalyst and the second metal catalyst is fixed to a support.

9. The method of claim 8, wherein the first metal catalyst comprising the support is used in an amount of 1 part by weight to 50 parts by weight based on 100 parts by weight of the terephthalic acid.

10. The method of claim 8, wherein the second metal catalyst comprising the support is used in an amount of 1 part by weight to 50 parts by weight based on 100 parts by weight of the terephthalic acid.

11. The method of claim 8, wherein the second metal catalyst comprises 0.5 wt % to 20 wt % of the ruthenium (Ru) compound.

12. The method of claim 8, wherein the support is a porous inorganic support having a specific surface area of 200 $m^2/g$ to 900 $m^2/g$.

13. The method of claim 8, wherein the support has a total pore volume of 1.2 $cm^3/g$ or less, and a volume of pores having a radius of 10 Å or less is in a range of 0.1 $cm^3/g$ to 0.8 $cm^3/g$.

14. The method of claim 8, wherein the support is Y-type zeolite.

15. The method of claim 3, wherein the reducing of the terephthalic acid is performed by contacting the terephthalic acid and hydrogen gas, and the reducing of the reduction product of the terephthalic acid is performed by contacting the reduction product of the terephthalic acid and hydrogen gas.

16. The method of claim 3, wherein the reducing of the terephthalic acid and the reducing of the reduction product of the terephthalic acid are respectively performed in a temperature range of 50° C. to 350° C.

17. The method of claim 3, wherein the reducing of the terephthalic acid and the reducing of the reduction product of the terephthalic acid are respectively performed at a pressure of 30 bar to 150 bar.

18. The method of claim 3, wherein the second metal catalyst comprises the ruthenium (Ru) compound, the tin (Sn) compound, and the platinum (Pt) compound in a weight ratio of 1:0.9 to 1.1:0.3 to 0.55.

19. The method of claim 3, wherein a molar ratio of trans-1,4-cyclohexanedimethanol in the finally generated 1,4-cyclohexanedimethanol is 20% or more.

20. An apparatus for preparing 1,4-cyclohexanedimethanol by reducing terephthalic acid, the apparatus comprising:
a reactor including a raw material feeding unit in which terephthalic acid is transferred and introduced into a top end, a reaction section in which a reduction reaction of the terephthalic acid introduced from the raw material feeding unit is performed, and an outlet which is formed at a bottom end to allow a product generated in the reaction section to be transferred to a receiver;
a preheater in which the terephthalic acid and ion exchange water are introduced to transfer dissolved terephthalic acid to the reactor by an inert gas through a mass flow controller; and
the receiver which recovers the product from the outlet from which the product generated in the reaction section is discharged,
wherein the reaction section comprises an upper reaction section, in which a first metal catalyst including a palladium (Pd) compound is injected to perform a reduction reaction of the terephthalic acid introduced from the raw material feeding unit, and a lower reaction section in which a second metal catalyst, as a catalyst including a ruthenium (Ru) compound, a tin (Sn) compound, and a platinum (Pt) compound, is injected to form an interface with the first metal catalyst and perform a reduction reaction of a resultant product reduced in the upper reaction section.

* * * * *